(12) United States Patent
Lal et al.

(10) Patent No.: US 7,268,245 B2
(45) Date of Patent: Sep. 11, 2007

(54) MULTINUCLEAR PLATINUM COMPOUNDS

(75) Inventors: Manjari Lal, Redmond, WA (US); Lynn C. Gold, Seattle, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 0 days.

(21) Appl. No.: 11/550,546

(22) Filed: Oct. 18, 2006

(65) Prior Publication Data

US 2007/0129431 A1 Jun. 7, 2007

Related U.S. Application Data

(63) Continuation-in-part of application No. 11/080,348, filed on Mar. 14, 2005, now Pat. No. 7,129,368.

(60) Provisional application No. 60/753,915, filed on Dec. 22, 2005, provisional application No. 60/659,932, filed on Mar. 10, 2005, provisional application No. 60/553,108, filed on Mar. 15, 2004.

(51) Int. Cl.
*C07F 15/00* (2006.01)
*A61K 31/28* (2006.01)

(52) U.S. Cl. ...................................... 556/137; 514/492
(58) Field of Classification Search ................ 556/137; 514/492

See application file for complete search history.

(56) References Cited

U.S. PATENT DOCUMENTS 7,129,368 B2 * 10/2006 Lal ............................. 556/137

OTHER PUBLICATIONS

Kortes et al., Inorganic Chemistry, vol. 38, No. 22, pp. 5045-5052 (1999).*
Lin et al., Inorganica Chimica Acta, vol. 271, No. 1-2, pp. 124-128 (1998).*

* cited by examiner

*Primary Examiner*—Porfirio Nazario-Gonzalez
(74) *Attorney, Agent, or Firm*—Christensen O'Connor Johnson Kindness PLLC

(57) ABSTRACT

Multinuclear platinum compounds, compositions that include the platinum compounds, methods for making the platinum compounds, and methods for treating cellular proliferative diseases by administering the platinum compounds.

29 Claims, No Drawings

MULTINUCLEAR PLATINUM COMPOUNDS

CROSS-REFERENCES TO RELATED APPLICATIONS

This application claims the benefit of U.S. Provisional Application No. 60/753,915, filed Dec. 22, 2005, and is a continuation-in-part of U.S. patent application Ser. No. 11/080,348, filed Mar. 14, 2005 now U.S. Pat. No. 7,129,368, which claims the benefit of U.S. Provisional Application No. 60/659,932, filed Mar. 10, 2005, and U.S. Provisional Application No. 60/553,108, filed Mar. 15, 2004.

BACKGROUND OF THE INVENTION

Cisplatin, cis-[PtCl$_2$(NH$_3$)$_2$], is one of the most widely used anti-tumor drugs. Cisplatin is a square-planar Pt (II) complex featuring two inert Pt—N bonds and two relatively labile Pt—Cl bonds. The electrophilic character of the central platinum atom allows cis-[PtCl$_2$(NH$_3$)$_2$] to enter a cell to react with nucleophilic groups of the cellular components. A number of observations indicate that the anti-tumor activity of cisplatin is related to its ability to bind to DNA through sequential replacements of the chloride ligands by the N$_7$ atoms of the guanine or the adenine bases.

The Physicians' Desk Reference reports that cisplatin (commercial name, Platinol) can be used to treat testicular, ovarian, and bladder cancers. Methods of treating cancer using cisplatin and cisplatin analogs are described in U.S. Pat. No. 4,177,263, among other publications. Cisplatin is administered intravenously and is transported throughout the body by the blood stream. Cisplatin reaches cancer cells mainly as a neutral molecule and is believed to enter the cell mainly through passive diffusion. Inside the cell, hydrolysis replaces one or both chlorines with water molecules (aquation). The intermediate monoaquated species, [PtCl(H$_2$O)(NH$_3$)$_2$]$^+$, is the most active/reactive species responsible for the cytotoxic action of cisplatin. The final product of cisplatin hydrolysis is [Pt(OH)$_2$(NH$_3$)$_2$], which is inactive.

Cisplatin, although a very potent and successful antineoplastic, is very toxic. Nephrotoxicity and ototoxicity are dose-limiting factors, and other toxic manifestations include severe nausea and vomiting. The severe toxicity of cisplatin coupled with the development over time of cisplatin-resistant tumors has led to the search for, and development of, improved platinum-based drugs. Desired properties of new and improved platinum drugs include a broader spectrum of activity, particularly against cisplatin-resistant tumors (e.g., lung, breast, and colon cancers); an improved therapeutic index, either through greater efficacy or reduced toxicity; and/or modified pharmacological properties to improve drug delivery.

Several second generation platinum anti-cancer compounds, for example, carboplatin (cis-diamine[1,1-cyclobutanedicarboxylato(2-)]-O,O'-platinum (II)), oxaliplatin, iproplatin, and tetraplatin, have been developed. Carboplatin was the second platinum anticancer drug to be approved for clinical use and is less toxic than cisplatin. However, carboplatin is also less active against tumors, requiring higher dosing, and is affected by the same resistance mechanism. Iproplatin and tetraplatin are as active as carboplatin, but are more toxic. Oxaliplatin is more toxic than carboplatin, but has shown promising activity in gastrointestinal tumors, in patients with ovarian cancer who have previously received cisplatin, and in advanced, cisplatin-resistant non-small cell lung patients.

Limitations in second generation platinum drugs have led to the development of third generation compounds, including chelates containing 1,2-diaminocyclohexane (DACH), and promising non-classic (trans- and multinuclear) platinum complexes.

Multinuclear platinum compounds represent innovative structures designed and investigated with the aim of discovering new platinum compounds that are structurally dissimilar to cisplatin and possibly characterized by innovative mechanisms of DNA interaction. Various multinuclear platinum complexes with anti-cancer activity have been described and are currently in clinical trials. One example of a multinuclear platinum compound is BBR3464 (see U.S. Pat. No. 6,011,166; Manzotti et al., *Cancer Res.* 6:2626, 2000). In preclinical studies, BBR3464 exhibited a very high biological activity against cisplatin-resistant tumor cell lines, but toxic side effects were dose limiting. Fewer than 1% of the platinum complexes tested for pre-clinical anti-cancer activity have entered clinical trials in the past 20 years (Perez et al., *Curr. Med. Chem.-Anti-Cancer Agents* 2 (4): 539:551, 2002).

Accordingly, despite the advances that have been made in the development of alternative platinum compounds, there exists is a need in the art for platinum compounds that are as active as cisplatin, have lower toxicity than cisplatin, and that are effective against cisplatin resistant tumors.

SUMMARY

The present invention provides multinuclear platinum compounds, compositions that include the platinum compounds, methods for making the platinum compounds, and methods of treating cancer using the platinum compounds.

In one aspect of the invention, platinum compounds are provided. The platinum compounds are multinuclear platinum compounds in which the platinum atoms are covalently coordinated through aminoacetic acid groups. In one embodiment, dinuclear platinum compounds are provided. In one embodiment, trinuclear compounds are provided. In one embodiment, tetranuclear compounds are provided.

In one embodiment, the invention provides diplatinum diaminetetraacetic acid compounds having formula (I):

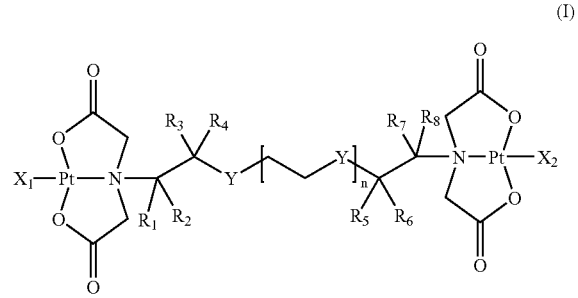

wherein, $R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

Y at each occurrence is independently selected from O and $NR_9$, wherein $R_9$ is selected from hydrogen, substituted and unsubstituted alkyl, and substituted and unsubstituted acyl;

n is 0, 1, 2, 3, 4, or 5; and $X_1$ and $X_2$ are independently selected from ammonia, amino, nitro, C1-C6 alkoxy, hydroxy, chloride, bromide, and iodide.

In another embodiment, the invention provides diplatinum diamine tetraacetic acid compounds having formula (II):

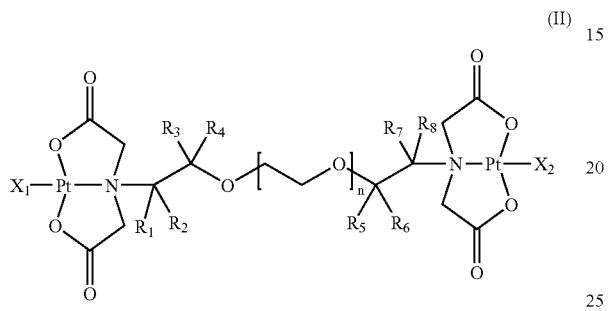

wherein, $R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

n is 0, 1, 2, 3, 4, or 5; and $X_1$ and $X_2$ are independently selected from ammonia, amino, nitro, C1-C6 alkoxy, hydroxy, chloride, bromide, and iodide.

In another embodiment, the invention provides diplatinum diamine tetraacetic acid compounds having formula (III):

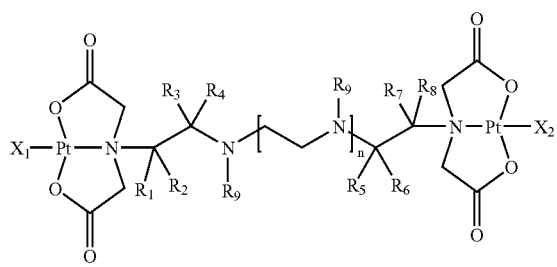

wherein, $R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

$R_9$ at each occurrence is independently selected from hydrogen and substituted and unsubstituted alkyl, and substituted and unsubstituted acyl;

n is 0, 1, 2, 3, 4, or 5; and $X_1$ and $X_2$ are independently selected from ammonia, amino, nitro, C1-C6 alkoxy, hydroxy, chloride, bromide, and iodide.

In another embodiment, the invention provides diplatinum diamine tetraacetic acid compounds having formula (IV):

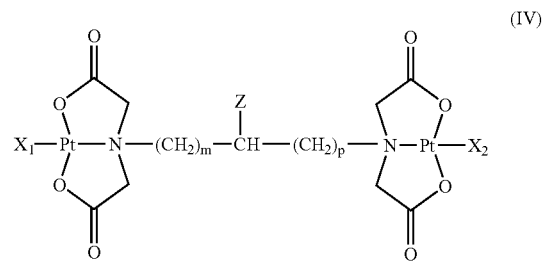

wherein, m is 1, 2, 3, 4, 5, or 6;

p is 1, 2, 3, 4, 5, or 6;

Z is selected from $OR_{10}$ and $NR_{11}R_{12}$, wherein $R_{10}$, $R_{11}$, and $R_{12}$ are selected from hydrogen and substituted and unsubstituted alkyl; and $X_1$ and $X_2$ are independently selected from ammonia, amino, nitro, C1-C6 alkoxy, hydroxy, chloride, bromide, and iodide.

In another embodiment, the invention provides polynuclear platinum compounds having formula (V):

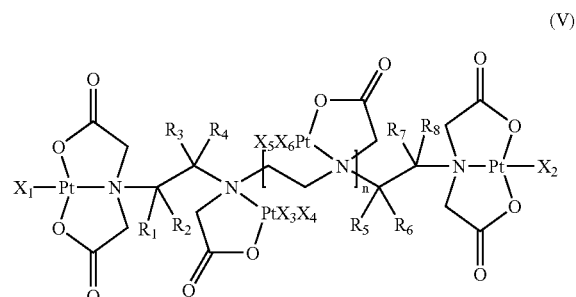

wherein, $R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

n is 0, 1, 2, 3, 4, or 5; and $X_1$, $X_2$, $X_3$, $X_4$, $X_5$, and $X_6$ are independently selected from ammonia, amino, nitro, C1-C6 alkoxy, hydroxy, chloride, bromide, and iodide.

In another aspect, the invention provides methods for making the platinum compounds.

In a further aspect, the invention provides compositions that include a platinum compound of the invention (e.g., compounds having formulas (I)-(V)). The compositions include one or more of the platinum compounds, a pharmaceutically acceptable carrier or diluent, and optionally, one or more additional therapeutic agents. The compositions are useful for the administration of platinum compounds to treat cancer.

In another aspect of the invention, methods for treating cancer by administration of a platinum compound of the invention (e.g., compounds having formulas (I)-(V)) are provided. In the method, a therapeutically effective amount of a platinum compound of the invention is administered to a subject in need thereof.

DETAILED DESCRIPTION OF THE INVENTION

The present invention provides multinuclear platinum compounds useful as anticancer agents, compositions that include the platinum compounds, methods for making the platinum compounds, and methods of treating cancer using the platinum compounds. As used herein, the term "multinuclear platinum compound" refers to a compound that includes two or more platinum atoms.

In one aspect of the invention, dinuclear platinum compounds are provided. As used herein, the term "dinuclear platinum compound" refers to a compound that includes two platinum atoms. The platinum compounds of the invention are platinum carboxylate compounds in which platinum is covalently coordinated through one or more carboxylate groups.

In one embodiment, the platinum compounds are diplatinum diamine tetraacetic acid compounds. As used herein, the term "diplatinum diamine tetraacetic acid compound" refers to a compound that includes two platinum atoms and a linker moiety having two aminodiacetic acid (i.e., —N(CH$_2$CO$_2$)$_2$) groups in which the platinum atoms are coordinated by one or more of the aminoacetic acid groups.

In one embodiment, the invention provides diplatinum diaminetetraacetic acid compounds having formula (I):

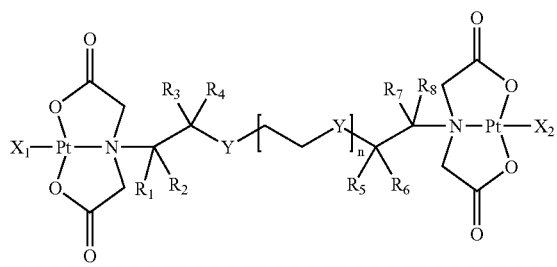

wherein,

R$_1$, R$_2$, R$_3$, R$_4$, R$_5$, R$_6$, R$_7$, and R$_8$ are independently selected from hydrogen, substituted and unsubstituted aryl, substituted and unsubstituted alkyl, and substituted and unsubstituted cycloalkyl, or R$_1$, R$_2$, R$_3$, and R$_4$ together with the carbons atoms to which they are attached form a substituted and unsubstituted benzene ring, or R$_5$, R$_6$, R$_7$, and R$_8$ together with the carbons atoms to which they are attached form a substituted and unsubstituted benzene ring;

Y at each occurrence is independently selected from O and NR$_9$, wherein R$_9$ is selected from hydrogen, substituted and unsubstituted alkyl, and substituted and unsubstituted acyl;

n is 0, 1, 2, 3, 4, or 5; and

X$_1$ and X$_2$ are independently selected from ammonia, amino, nitro, C1-C6 alkoxy, hydroxy, chloride, bromide, and iodide.

In one embodiment, Y is O.

In one embodiment, Y is N and R$_9$ is selected from CH$_2$OH, CH$_2$NH$_2$, CH$_2$CO$_2$H, and C(=O)-nC$_{10}$H$_{21}$-nC$_{17}$H$_{35}$.

In one embodiment, R$_1$-R$_8$ are hydrogen.

In one embodiment, X$_1$ and X$_2$ are chloride.

In one embodiment, alkyl is substituted or unsubstituted C$_1$-C$_{17}$ alkyl.

In one embodiment, cycloalkyl is substituted or unsubstituted C$_3$-C$_7$ cycloalkyl.

In another embodiment, the invention provides diplatinum diamine tetraacetic acid compounds having formula (II):

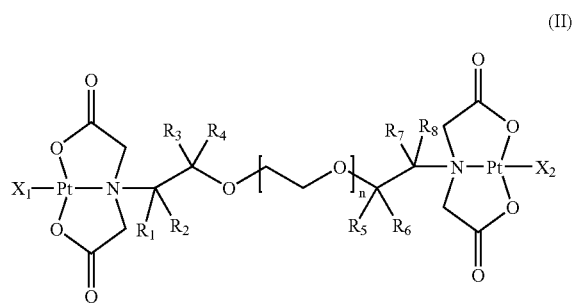

wherein,

R$_1$, R$_2$, R$_3$, R$_4$, R$_5$, R$_6$, R$_7$, and R$_8$ are independently selected from hydrogen, substituted and unsubstituted aryl, substituted and unsubstituted alkyl, and substituted and unsubstituted cycloalkyl, or R$_1$, R$_2$, R$_3$, and R$_4$ together with the carbons atoms to which they are attached form a substituted and unsubstituted benzene ring, or R$_5$, R$_6$, R$_7$, and R$_8$ together with the carbons atoms to which they are attached form a substituted and unsubstituted benzene ring;

n is 0, 1, 2, 3, 4, or 5; and

X$_1$ and X$_2$ are independently selected from ammonia, amino, nitro, C1-C6 alkoxy, hydroxy, chloride, bromide, and iodide.

In one embodiment, R$_1$-R$_8$ are hydrogen.

In one embodiment, n is 1.

In one embodiment, n is 1 and R$_1$-R$_8$ are hydrogen.

In one embodiment, n is 1, R$_1$, R$_2$, R$_3$, and R$_4$ together with the carbons atoms to which they are attached form a benzene ring, and R$_5$, R$_6$, R$_7$, and R$_8$ together with the carbons atoms to which they are attached form a benzene ring.

In another embodiment, the invention provides diplatinum diamine tetraacetic acid compounds having formula (III):

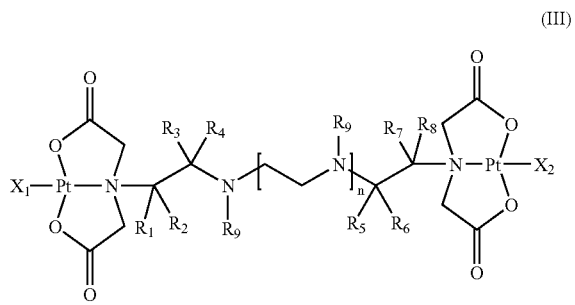

(III)

wherein, $R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

$R_9$ at each occurrence is independently selected from hydrogen and substituted and unsubstituted alkyl, and substituted and unsubstituted acyl;

n is 0, 1, 2, 3, 4, or 5; and $X_1$ and $X_2$ are independently selected from ammonia, amino, nitro, C1-C6 alkoxy, hydroxy, chloride, bromide, and iodide.

In one embodiment, $R_1$-$R_8$ are hydrogen.

In one embodiment, $R_9$ is selected from $CH_2OH$, $CH_2NH_2$, $CH_2CO_2H$, and $C(=O)$-$nC_{10}H_{21}$-$nC_{17}H_{35}$.

In one embodiment, n is 0.

In one embodiment, n is 1.

In one embodiment, n is 0, $R_1$-$R_8$ are hydrogen, and $R_9$ is $CH_2CO_2H$.

In one embodiment, n is 1, $R_1$-$R_8$ are hydrogen, and $R_9$ is $CH_2CO_2H$.

In another embodiment, the invention provides diplatinum diamine tetraacetic acid compounds having formula (IV):

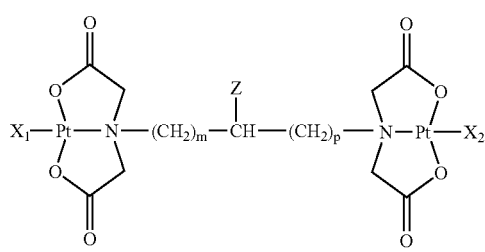

(IV)

wherein, m is 1, 2, 3, 4, 5, or 6;

p is 1, 2, 3, 4, 5, or 6;

Z is selected from $OR_{10}$ and $NR_{11}R_{12}$, wherein $R_{10}$, $R_{11}$, and $R_{12}$ are selected from hydrogen and substituted and unsubstituted alkyl; and $X_1$ and $X_2$ are independently selected from ammonia, amino, nitro, C1-C6 alkoxy, hydroxy, chloride, bromide, and iodide.

In one embodiment, m is 1.

In one embodiment, p is 1.

In one embodiment, Z is OH.

In one embodiment, m is 1, p is 1, and Z is OH.

In one embodiment, the compounds of the invention include a functional group (i.e., substituent) that can be used to further modify the platinum compound. Representative functional groups include hydroxy groups (—OH), amino groups (—$NH_2$, NHR, and $NR_2$, where R is an alkyl or aryl group), sulfhydryl groups (—SH), and carboxy groups (—$CO_2H$).

In another aspect, the invention provides polynuclear platinum compounds. As used herein, the term "polynuclear platinum compound" refers to a compound that includes more than two platinum compounds, wherein each platinum is covalently coordinated through one or more aminoacetic acid groups.

In one embodiment, the polynuclear platinum compounds are trinuclear platinum compounds (n=0). In one embodiment, the polynuclear platinum compounds are tetranuclear platinum compounds (n=1).

In one embodiment, the invention provides polynuclear platinum compounds having formula (V):

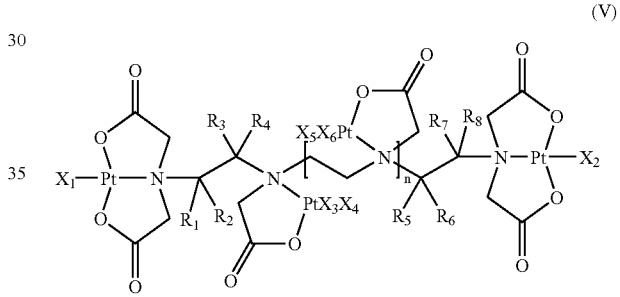

(V)

wherein, $R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

n is 0, 1, 2, 3, 4, or 5; and $X_1$, $X_2$, $X_3$, $X_4$, $X_5$, and $X_6$ are independently selected from ammonia, amino, nitro, C1-C6 alkoxy, hydroxy, chloride, bromide, and iodide.

In one embodiment, $R_1$-$R_8$ are hydrogen.

In one embodiment, n is 0. The preparation of a representative compound with n=0 is described in Example 8.

In one embodiment, n is 1. The preparation of a representative compound with n=1 is described in Example 9.

For the compounds described above, the term "alkyl" refers to C1-C17 straight chain and branched alkyl groups. Representative alkyl groups include, for example, methyl, ethyl, n-propyl, i-propyl, n-butyl, s-butyl, i-butyl, and t-butyl groups. The term "cycloalkyl" refers to C3-C7 cyclic alkyl groups. Representative cycloalkyl groups include, for example, cyclopropyl, cyclobutyl, cyclopentyl, cyclohexyl, and cycloheptyl groups. The term "aryl" refers to aromatic groups. Representative aryl groups include C6-C12 aryl groups, for example, phenyl, benzyl, and naphthyl groups. The term "acyl" refers to groups having the formula: —C(=O)—R, where R is an alkyl, cycloalkyl, or aryl group. In certain embodiments, these groups are unsubstituted. In other embodiments, one or more of the hydrogen atoms of these groups are substituted. Suitable substituents include alkyl, cycloalkyl, aryl, halo, hydroxy, amino, sulfhydryl, and carboxy groups. Exemplary substituted alkyl groups include fluorinated alkyl groups (e.g., trifluoromethyl), hydroxy alkyl groups (e.g., —CH$_2$OH), amino alkyl groups (e.g., —CH$_2$NH$_2$), and carboxy alkyl groups (e.g., —CH$_2$CO$_2$H).

In another aspect of the invention, methods for making the dinuclear platinum compounds are provided. The platinum compounds of the invention are prepared by reaction of a suitably reactive platinum compound with a polycarboxylic acid (or salt) having at least two aminodiacetic acid (i.e., —N(CH$_2$CO$_2$)$_2$) groups.

Suitably reactive platinum compounds are those platinum compounds that are reactive toward carboxylic acids (or their salts). Suitable platinum compounds include, for example, cis-diaminedichloroplatinum (II) (cisplatin), and compounds derived from cisplatin, for example, diaminedinitroplatinum (II), and diaminemonochloromononitroplatinum (II).

Suitable polycarboxylic acids having at least two aminodiacetic acid groups include, for example, ethylene glycol-bis-(β-aminoethyl)-N,N,N',N'-tetraacetic acid, diethylene triamine-N,N,N',N'',N''-pentaacetic acid, 1,3-diamino-2-hydroxypropyl-N,N,N',N'-tetraacetic acid, and triethylene tetraamine-N,N,N',N'',N''',N'''-hexaacetic acid.

In one aspect, the present invention provides a dinuclear platinum compound formed by combining a suitably reactive platinum compound (e.g., cis-diaminedinitroplatinum (II)) with a polycarboxylic acid (or salt) having at least two aminodiacetic acid groups (e.g., ethylene glycol-bis-(β-aminoethyl)-N,N,N',N'-tetraacetic acid).

Dinuclear platinum compounds of the invention are obtained by treating a suitably reactive polycarboxylic acid (or salt) having at least two aminodiacetic acid groups with cis-diaminedinitroplatinum (II). In the method, the polycarboxylic acid is treated with two equivalents of cis-diaminedinitroplatinum (II) to provide the dinuclear compound. In one embodiment, a solution of the polycarboxylic acid in 1N aqueous sodium hydroxide (pH about 6.5) is treated with a aqueous solution of cis-diaminedinitroplatinum (II), prepared by treating cis-diaminedichloroplatinum (II) with two equivalents silver nitrate in water and filtered to remove silver chloride. The reaction mixture is stirred and heated (e.g., 60° C.) to complete the reaction. The product dinuclear platinum compound can be isolated from the reaction mixture by precipitation by the addition of acetone to provide a white solid that can be collected by filtration or centrifugation, washed with acetone, and dried under vacuum.

In one embodiment, the present invention provides ethylene glycol-bis-(β-aminoethyl)-N,N,N',N'-tetraacetic-acid-diplatinum, which is the product resulting from the reaction of cisplatin with the tetrasodium salt of ethylene glycol-bis-(β-aminoethyl)-N,N,N',N'-tetraacetic acid (EGTA). The preparation of ethylene glycol-bis-(β-aminoethyl)-N,N,N', N'-tetraacetic-acid-diplatinum is described in Example 1. In the method, a solution of the tetrasodium salt of ethylene glycol-bis-(β-aminoethyl)-N,N,N',N'-tetraacetic acid in 1N aqueous sodium hydroxide (pH about 9) is treated with an aqueous solution of cis-diaminedichloroplatinum (II). The reaction mixture is stirred and heated (initial temperature of about 60° C.; then temperature lowered to about 50° C.) to complete the reaction. The product dinuclear platinum compound can be isolated from the reaction mixture by precipitation by the addition of acetone, and then dried under vacuum.

In another embodiment, the present invention provides 1,3-diamino-2-hydroxypropane-N,N,N',N'-tetraacetic-acid-diplatinum, which is the product resulting from the reaction of cis-diaminedinitroplatinum (II) with the tetrasodium salt of 1,3-diamino-2-hydroxypropane-N,N,N',N'-tetraacetic acid (DAPTA). The preparation of 1,3-diamino-2-hydroxypropane-N,N,N',N'-tetraacetic-acid-diplatinum is described in Example 2. In the method, a solution of the tetrasodium salt of 1,3-diamino-2-hydroxypropane-N,N,N', N'-tetraacetic acid in 1N aqueous sodium hydroxide (pH about 3) is treated with an aqueous solution of cis-diaminedinitroplatinum (II), prepared by treating cis-diaminedichloroplatinum (II) with silver nitrate in water and filtered to remove silver chloride. The reaction mixture is stirred and heated (initial temperature of about 60° C.; then heat removed) to complete the reaction at room temperature. The product dinuclear platinum compound can be isolated from the reaction mixture by precipitation by the addition of acetone, and then dried under vacuum. Alternatively, the synthesis can be carried out a pH of about 9.

In another embodiment, the present invention provides diethylene triamine-N,N,N',N'',N''-pentaacetic-acid-diplatinum, which is the product resulting from the reaction of the active cis-diaminedinitroplatinum (II) with the sodium salt of diethylene triamine-N,N,N',N'',N''-pentaacetic acid (DTPA). The preparation of diethylene triamine-N,N,N',N'', N''-pentaacetic-acid-diplatinum is described in Example 3. In the method, a solution of the tetrasodium salt of diethylenetriamine-N,N,N',N'',N''-pentaacetic acid in 1N aqueous sodium hydroxide (pH about 9) is treated with a aqueous solution of cis-diaminedinitroplatinum (II), prepared by treating cis-diaminedichloroplatinum (II) with silver nitrate in water and filtered to remove silver chloride. The reaction mixture is stirred and heated under nitrogen (initial temperature of about 60° C.; then heat removed) to complete the reaction at room temperature. The product dinuclear platinum compound can be isolated from the reaction mixture by precipitation by the addition of acetone, and then dried under vacuum.

In another embodiment, the present invention provides triethylene tetraamine-N,N,N',N'',N''',N'''-hexaacetic-acid-diplatinum, which is the product resulting from the reaction of the active cis-diaminedinitroplatinum (II) with the sodium salt of triethylene tetraamine-N,N,N',N'',N''',N'''-hexaacetic acid (TTHA). The preparation of triethylene-tetraamine-N, N,N',N'',N''',N'''-hexaacetic-acid-diplatinum is described in Example 4. In the method, a solution of the sodium salt of triethylene tetraamine-N,N,N',N'',N''',N'''-hexaacetic acid in 1N aqueous sodium hydroxide (pH about 9.5) is treated with a aqueous solution of cis-diaminedinitroplatinum (II), prepared by treating cis-diaminedichloroplatinum (II) with silver nitrate in water and filtered to remove silver chloride. The reaction mixture is stirred and heated at about 60° C. for four hours. The product dinuclear platinum compound can be isolated from the reaction mixture by precipitation by the addition of acetone, and then dried under vacuum.

In another aspect, the present invention provides methods of treating human or animal subjects suffering from a cellular proliferative disease, such as cancer. Representative cell proliferative diseases treatable by the compounds of the invention include hematologic cancers, such as leukemia, lymphoma, and myeloma, and nonhematologic cancers, such as solid tumor carcinomas (e.g., breast, ovarian, pancreatic, colon, colorectal, non-small lung, and bladder), sarcomas, and gliomas. The present invention provides methods of treating a human or animal subject in need of such treatment, comprising administering to the subject a therapeutically effective amount of one or more platinum compounds of the invention, either alone or in combination with one or more other therapeutic and/or anticancer agents.

The platinum compounds of the invention have cytotoxic activity against cancer cells. Example 10 describes the cytotoxicity of representative compounds of the invention. In some embodiments, representative platinum compounds of the invention have improved cytotoxic activities against cancer cells as compared to cisplatin or carboplatin as shown in Table 1.

In other aspects, the present invention provides methods for treating a cellular proliferative disease in a human or animal subject in need of such treatment, comprising administering to said subject an amount of a platinum compound of the invention effective to reduce or prevent cellular proliferation or tumor growth in the subject.

In yet other aspects, the present invention provides methods for treating a cellular proliferative disease in a human or animal subject in need of such treatment comprising administering to said subject an amount of a platinum compound of the invention effective to reduce or prevent cellular proliferation in the subject in combination with at least one additional agent for the treatment of cancer.

The platinum compounds of the invention, either alone or in combination with other anticancer agents, can be used for the prevention and treatment of cancers such as primary or metastatic melanoma, thymoma, lymphoma, sarcoma, lung cancer (NSCLC and SCLC), gastric cancer, liver cancer, non-Hodgkin's lymphoma, Hodgkin's lymphoma, leukemias, testicular cancer, uterine cancer, cervical cancer, bladder cancer, kidney cancer, colon cancer, colorectal cancer, and adenocarcinomas such as breast cancer, prostate cancer, ovarian cancer, and pancreatic cancer.

Compositions that include one or more platinum compounds of the invention are administered to deliver therapeutically effective amounts of the platinum compound. Therapeutically effective amounts of the platinum compound(s) will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the platinum compounds of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the platinum compounds of the invention may be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Platinum compounds that exhibit large therapeutic indices are particularly suitable in the practice of the methods of the invention. The data obtained from cell culture assays and animal studies may be used in formulating a range of dosage for use in humans or other mammals. The dosage of such platinum compounds lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The platinum compounds of the invention may be administered alone, or in combination with one or more additional therapeutically active agents. For example, in the treatment of cancer, the platinum compounds may be administered in combination with therapeutic agents including, but not limited to, androgen inhibitors, such as flutamide and luprolide; antiestrogens, such as tomoxifen; antimetabolites and cytotoxic agents, such as daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, streptozocin, bleomycin, dactinomycin, and idamycin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; and other antineoplastic agents, such as live *Mycobacterium bovis*, dicarbazine, asparaginase, leucovorin, mitotane, vincristine, vinblastine, and taxanes (e.g., paclitaxel, docetaxel). Appropriate amounts in each case will vary with the particular agent, and will be either readily known to those skilled in the art or readily determinable by routine experimentation.

Administration of the platinum compounds of the invention is accomplished by any effective route, for example, parenterally or orally. Methods of administration include inhalational, buccal, intramedullary, intravenous, intranasal, intrarectal, intraocular, intraabdominal, intraarterial, intraarticular, intracapsular, intracervical, intracranial, intraductal, intradural, intralesional, intramuscular, intralumbar, intramural, intraoperative, intraparietal, intraperitoneal, intrapleural, intrapulmonary, intraspinal, intrathoracic, intratracheal, intratympanic, intrauterine, intravascular, and intraventricular administration, and other conventional means. The platinum compounds of the invention may be injected directly into a tumor, into the vicinity of a tumor, or into a blood vessel that supplies blood to the tumor.

In other aspects, the present invention provides pharmaceutical compositions comprising at least one platinum compound of the invention together with a pharmaceutically acceptable carrier suitable for administration to a human or animal subject, either alone or together with other therapeutic and/or anticancer agents. The platinum compounds of the invention may be formulated into a composition that additionally comprises suitable pharmaceutically acceptable carriers, including excipients and other compounds that facilitate administration of the platinum compounds to a mammalian subject. Further details on techniques for formulation and administration may be found in the latest edition of Remington's Pharmaceutical Sciences, Maack Publishing Co, Easton Pa.

Compositions for oral administration may be formulated using pharmaceutically acceptable carriers well known in the art, in dosages suitable for oral administration. Such carriers enable the compositions containing platinum compounds of the invention to be formulated as tablets, pills, dragees, capsules, liquids, gels, syrups, slurries, and suspensions, suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins, such as gelatin and collagen. If desired, disintegrating or solubilizing agents may be added, such as the crosslinked polyvinyl pyrrolidone, agar, alginic acid, or a salt thereof, such as sodium alginate. Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Platinum compounds for oral administration may be formulated, for example, as push-fit capsules made of gelatin, as well as soft, sealed capsules made of gelatin and a coating such as glycerol or sorbitol. Push-fit capsules may contain platinum compounds mixed with filler or binders such as lactose or starches, lubricants such as talc or magnesium stearate, and, optionally, stabilizers. In soft capsules, the platinum compounds may be dissolved or suspended in suitable liquids, such as fatty oils, liquid paraffin, or liquid polyethylene glycol with or without stabilizers.

Compositions for parenteral administration include aqueous solutions of one or more platinum compounds of the invention. For injection, the platinum compounds may be formulated in aqueous solutions, such as in physiologically compatible buffers such as Hank's solution, Ringer's solution, or dextrose solutions. Aqueous injection suspensions may contain substances, which increase the viscosity of the suspension, such as sodium carboxymethyl cellulose, sorbitol, or dextran.

Compositions containing the platinum compounds of the present invention may be manufactured in a manner similar to that known in the art (e.g., by means of conventional mixing, dissolving, granulating, dragee-making, levigating, emulsifying, encapsulating, entrapping, and lyophilizing processes). The compositions may also be modified to provide appropriate release characteristics (e.g., sustained release or targeted release) by conventional means (e.g., coating).

Compositions containing the platinum compounds may be provided as a salt and can be formed with many acids including, but not limited to, hydrochloric, sulfuric, acetic, lactic, tartaric, malic, and succinic acids. Salts tend to be more soluble in aqueous or other protic solvents than are the corresponding free base forms.

After compositions formulated to contain the platinum compounds and an acceptable carrier have been prepared, they can be placed in an appropriate container and labeled for use.

In another aspect of the invention, a kit is provided that includes one or more platinum compounds of the invention in one or more containers. A representative kit includes a container that includes a quantity of a platinum compound and a package insert or other labeling including directions for treating a cellular proliferative disease by administering a quantity of the compound.

The following examples are provided for the purpose of illustrating, not limiting, the invention.

EXAMPLES

Example 1

Preparation of Ethylene Glycol-bis-(β-aminoethyl)-N,N,N',N'-tetraacetic-acid-diplatinum To cisplatin (Saiquest, India) ([Pt(NH$_3$)$_2$Cl$_2$]) solid (1 g) was added 100 ml water with constant stirring. The entire solution was kept under stirring at about 60° C. until a clear solution was obtained (about 30 minutes).

Ethylene glycol-bis-(β-aminoethyl)-N,N,N',N'-tetraacetic-acid (EGTA) Acros Organics, Belgium) (0.426 g) was neutralized to pH about 9 using 1N NaOH (5 ml) to yield a clear solution, which was then diluted to 50 ml with water. The resulting sodium ethylene glycol-bis-(β-aminoethyl)-N,N,N',N'-tetraacetate solution (1 ml) was added dropwise to the cisplatin solution prepared as described above. The reaction mixture was stirred at about 60° C. for 3 hours. The temperature was then lowered to about 50° C., and the solution was allowed to stir for another 3 hours. The reaction mixture was refrigerated overnight. The solution was filtered using a 0.45 micron filter to remove any residual cisplatin.

The reaction mixture filtrate prepared as described above was precipitated using acetone. The precipitate was extracted by centrifugation (6000 rpm). The product was allowed to air dry at room temperature overnight. The following day the precipitate was vacuum dried.

IRv$_{max}$(KBr): 3236, 2878, 1658, 1578 cm$^{-1}$.

Example 2

Preparation of 1,3-Diamino-2-hydroxypropane-N,N,N',N'-tetraacetic-acid-diplatinum Method A. Silver nitrate (Aldrich) solution (0.717 g dissolved in 75 ml water) was added to cisplatin (Saiquest, India) ([Pt(NH$_3$)$_2$Cl$_2$]) solid (0.709 g) dropwise with constant stirring. The entire solution was stirred at about 70° C. until silver chloride precipitation was complete (about two hours). The solution was then filtered using a 0.45 micron disposable filter.

1,3-Diamino-2-hydroxypropane-N,N,N',N'-tetraacetic-acid (DAPTA) (Aldrich) (0.693 g) was neutralized to pH about 3 using 1N NaOH (3 ml) to yield a clear solution, which was then diluted to 70 ml with water. Cisplatin diaminedinitrate platinum (II) solution prepared as described above was added dropwise to the sodium diaminopropyl-N,N,N',N'-tetraacetate solution. The reaction mixture was stirred at about 60° C. for 2 hours. The heat was removed and the solution was stirred at room temperature overnight, and then filtered.

The reaction mixture filtrate prepared as described above was precipitated using acetone. The precipitate was extracted by centrifugation (6000 rpm) and then vacuum dried.

Method B. An alternative synthesis was performed according to the steps of Method A; except that the reaction was carried out at pH about 9.

IR$v_{max}$(KBr): 3185, 1601, 1387 cm$^{-1}$.

Example 3

Preparation of Diethylenetriamine-N,N,N',N'',N''-pentacetic-acid-diplatinum

Silver nitrate (Aldrich) solution (0.794 g dissolved in 80 ml water) was added to cisplatin (Saiquest, India) ([Pt(NH$_3$)$_2$Cl$_2$]) solid (0.709 g) dropwise with constant stirring. The entire solution was stirred at about 70° C. until silver chloride precipitation was complete (about two hours). The solution was then filtered using a 0.45 micron disposable filter.

Diethylenetriamine-N,N,N',N'',N''-pentaacetic acid (DTPA) (Aldrich) (0.464 g) was neutralized to pH about 9 using 1N NaOH (4 ml) to yield a clear solution, which was then diluted to 50 ml with water. The cisplatin diaminedinitrate platinum (II) solution prepared as described above was added dropwise to the sodium diethylenetriamine-N,N,N',N'',N''-pentaacetate solution. The reaction mixture was stirred under nitrogen atmosphere at about 60° C. for 2 hours. The heat was removed and the solution was stirred at room temperature overnight under nitrogen, and then filtered.

The reaction mixture filtrate prepared as described above was precipitated using acetone. The precipitate was extracted by centrifugation (6000 rpm) and then vacuum dried.

IR$v_{max}$(KBr): 3157,1597,1374 cm$^{-1}$.

Example 4

Preparation of Triethylene-N,N,N',N'',N''',N'''-tetraamine-hexaacetic-acid-diplatinum Silver nitrate (Aldrich) solution (0.56 g dissolved in 100 ml water) was added to cisplatin (Saiquest, India) ([Pt(NH$_3$)$_2$Cl$_2$]) solid (0.5 g) dropwise with constant stirring. The entire solution was stirred at about 60° C. for about two hours. The solution was then filtered using a 0.45 micron disposable filter. The filtrate was again heated and stirred at about 60° C. for another 30 minutes and then filtered again.

Triethylene tetraamine-N,N,N',N'',N''',N'''-hexaacetic acid (TTHA) (Aldrich) (0.412 g) was neutralized to pH about 9.5 using 1N NaOH (4 ml) and then diluted to 40 ml with water. The resulting sodium triethylene tetraamine-N,N,N',N'',N''',N'''-hexaacetate solution (1 ml) was added dropwise to the cisplatin prepared as described above. The reaction mixture was stirred at about 60° C. for 4 hours. The heat was removed and the reaction mixture was allowed to cool to room temperature. The solution was filtered using a 0.45 micron filter.

The reaction mixture filtrate prepared as described above was precipitated using acetone. The precipitate was extracted by centrifugation (6000 rpm). The precipitate was vacuum dried overnight.

Example 5

Preparation of Butylenebis(oxyethylenenitrilo)tetraacetic acid diplatinum

Cisplatin ([Pt(NH$_3$)$_2$Cl$_2$]) solid (0.8 g) is dissolved in 100 ml of water in a conical flask with constant stirring and the entire solution is allowed to stir at about 60° C. until a clear solution is obtained. This step takes about half an hour.

Butylenebis(oxyethylenenitrilo)tetraacetic acid (0.544 gm) is neutralized to pH about 9 using 1N NaOH (~10 ml) to obtain a clear solution. This solution is then diluted to about 50 ml with water. This solution is then added dropwise (about 1 ml) to the cisplatin solution prepared above maintained at about 60° C. The entire reaction mixture is allowed to stir at this temperature (about 60° C.) for about 3 hours. The temperature is then reduced to about 50° C. and the reaction mixture is allowed to stir at this temperature for another 3 hours.

After a total of 6 hours, this reaction mixture is refrigerated overnight to facilitate precipitation of unreacted cisplatin.

The next day, the refrigerated solution is filtered using 0.45 micron filter to remove unreacted cisplatin (if any). The filtrate containing the product is then precipitated by addition of acetone. The precipitate is then extracted by centrifugation and is allowed to dry overnight at room temperature. This is followed by vacuum drying to yield dry crystalline product.

Example 6

Preparation of Cyclohexyl-diethylenetriamine-pentaacetic acid diplatinum

Cisplatin ([Pt(NH$_3$)$_2$Cl$_2$]) solid (0.5 g) is dissolved in 50 ml of water in a conical flask with constant stirring and the entire solution is allowed to stir at about 60° C. until a clear solution is obtained. This step takes about half an hour.

Cyclohexyl-diethylenetriamine-pentaacetic acid (0.37 gm) is neutralized to pH about 9 using 1N NaOH (about 3 ml) to obtain a clear solution. This solution is then diluted to about 40 ml with water. This solution is then added dropwise (about 1 ml ) to the cisplatin solution prepared above maintained at about 60° C. The entire reaction mixture is allowed to stir at this temperature (about 60° C.) for about 3 hours. The temperature is then reduced to about 50° C. and the reaction mixture is allowed to stir at this temperature for another 3 hours.

After a total of 6 hours, this reaction mixture is refrigerated overnight to facilitate precipitation of unreacted cisplatin.

The next day, the refrigerated solution is filtered using 0.45 micron filter to remove unreacted cisplatin (if any). The filtrate containing the product is then precipitated by addition of acetone. The precipitate is then extracted by centrifugation and is allowed to dry overnight at room temperature. This is followed by vacuum drying to yield dry crystalline product.

Example 7

Preparation of 1,2-bis-2-aminophenoxyethane-N,N, N',N'-tetraacetic acid diplatinum Cisplatin (0.51 g) was dissolved in water (50 ml) with constant stirring at 70° C. The reaction mixture was left stirring at this temperature for 1 hour. After 1 hour a clear solution obtained and temperature was reduced to 60° C. 1,2-bis-2-Aminophenoxyethane-N,N,N',N'-tetraacetic acid (BAPTA) tetrasodium salt (0.47 gm) was dissolved directly into the cisplatin solution with constant stirring at 60° C. This reaction mixture was left stirring at this temperature for total of 6 hours. After 6 hours, heat was turned off and the reaction mixture was stirred until the temperature of the solution was reached room temperature following which the mixture was refrigerated (4° C.) to precipitate any unreacted cisplatin. The next day the refrigerated solution was filtered and then acetone (1:5) added to precipitate the product. The white precipitate obtained was centrifuged (6000 rpm, 25° C.), followed by several washings (5×) with acetone (50 ml). The product was left to air dry at room temperature followed by vacuum drying overnight.

Example 8

Preparation of Diethylenetriamine-N,N,N',N'',N''-pentaacetic-acid-triplatinum Cisplatin ($[Pt(NH_3)_2Cl_2]$) solid (0.814 g) was dissolved in 90 ml of water in a conical flask with constant stirring and the entire solution was allowed to stir at about 70° C. until a clear solution was obtained (about 30 minutes), then the tmeperature was reduced to about 60° C.

Diethylenetriamine-N,N,N',N'',N''-pentaacetic acid (DTPA) (Aldrich) (0.355 g) was neutralized to pH about 9 using 1N NaOH (3.5 ml) to yield a clear solution, which was then diluted to 25 ml with water. The sodium salt of DTPA was then added dropwise (1 ml) to the cisplatin solution maintained at 60° C. for about 6 hours and the progress of the reaction was monitored by observing the disappearance of cisplatin by thin layer chromatocgraphy. After 6 hours, the reaction mixture was cooled to room temperature and was filtered using 0.45 μm filter. The filterate was left at 4° C. in the refrigerator for 24 hours to precipitate any unreacted cisplatin. After 24 hours, there was no precipitation observed in the refrigerated sample. The solution was again filtered using 0.45 μm filtered followed by precipitation using acetone. The precipitate was extracted by centrifugation (6000 rpm) and then vacuum dried to provide diethylenetriamine-N,N,N',N'',N''-pentaacetic-acid-triplatinum (DTPA-triplatinum).

The cytotoxicity of DTPA-triplatinum was determined by the method described in Example 10. DTPA-triplatinum was found to have a $GI_{50}$ of 19 μM for A2780, compared to 15 μM cisplatin. DTPA-triplatinum was found to have a $GI_{50}$ of 63 μM for A2780 (platinum resistant), compared to 57 μM cisplatin.

Example 9

Preparation of Triethylenetetraamine-N,N,N',N'',N''', N''''-hexaacetic-acid-tetraplatinum Cisplatin ($[Pt(NH_3)_2Cl_2]$) solid (0.903 g) was dissolved in 100 ml of water in a conical flask with constant stirring and the entire solution was allowed to stir at about 70° C. until a clear solution is obtained (about 30 minutes).

Triethylene tetraamine-N,N,N',N'',N''',N''''-hexaacetic acid (TTHA) (Aldrich) (0.3713 g) was neutralized to pH about 9.5 using 1N NaOH (3.7 ml) and then diluted to 40 ml with water. The resulting sodium triethylene tetraamine-N, N,N',N'',N''',N''''-hexaacetate solution (1 ml) was added dropwise to the cisplatin solution prepared as described above. The reaction mixture was stirred at about 60° C. for about 6 hours. Heating was discontinued and the reaction mixture was allowed to cool to room temperature. The solution was filtered using a 0.45 micron filter.

The reaction mixture filtrate prepared as described above was precipitated using acetone. The precipitate was extracted by centrifugation (6000 rpm). The precipitate was vacuum dried overnight to yield to provide triethylenetetraamine-N,N,N',N'',N''',N''''-hexaacetic-acid-tetraplatinum (TTHA-tetraplatinum) as a pale white powder.

The cytotoxicity of TTHA-tetraplatinum was determined by the method described in Example 10. TTHA-tetraplatinum was found to have a $GI_{50}$ of 7 μM for A2780, compared to 15 μM cisplatin. TTHA-tetraplatinum was found to have a $GI_{50}$ of 50 μM for A2780 (platinum resistant), compared to 57 μM cisplatin.

Example 10

Cytotoxic Screening of Representative Platinum Compounds

Cytotoxicity was tested for cisplatin and representative compounds by measuring the amount of compound required to inhibit cell growth by 50% ($GI_{50}$ value). The representative compounds tested were ethylene glycol-bis-(β-aminoethyl)-N,N,N',N'-tetraacetic-acid-diplatinum (EGTA-diplatinum), prepared as described in Example 1; diaminopropyl-N,N,N',N'-tetraacetic-acid-diplatinum (DAPTA-diplatinum), prepared as described in Example 2; diethylenetriamine-N,N,N',N'',N''-pentaacetic-acid-diplatinum (DTPA-diplatinum), prepared as described in Example 3; and triethylene-tetraamine-N,N,N',N'',N''',N''''-hexaacetic-acid-diplatinum (TTHA-diplatinum) prepared as described in Example 4. Cytotoxicity was measured in six cell lines: two colorectal carcinoma cell lines (HT29 and HCT-116); two small cell lung cancer cell lines (NCI-H69 and NCI-H69/AR); and two ovarian cancer cell lines (A2780 and A2780/DPPt). Viable cell number was measured using the MTS cell viability assay (CELLTITER 96 $AQ_{ueous}$ One Solution Cell Proliferation Assay kit available from Promega, US). Cell growth inhibition was quantified by measuring absorbance at 490 nm, which is directly proportional to the number of living cells in culture.

The representative compounds were prepared as 10 mM stock solutions in water containing 5% dextrose (D5W). Cisplatin was prepared in saline. Dosing solutions were prepared by serial dilution of the stock solutions in cell culture medium to provide final concentrations of 0.006-100 μM.

All tumor lines were propagated under sterile conditions and incubated at 37° C. in HEPA-filtered $CO_2$ tissue culture incubators with 5% $CO_2$ and 95% humidity in colorless RPMI 1640 medium (Mediatech, Herndon, Va.) containing 5% fetal bovine serum (complete medium). The ovarian and colon tumor cell lines were plated in microtiter plates at a density of 5,000 cells per well. The lung lines were plated at a density of 10,000 cells per well.

Viable cell number was measured by the MTS dye conversion assay after a total of 72 hours of treatment. Sample wells were treated with 20 μl of the MTS solution warmed to 37° C. The plates were incubated for four hours at 37° C. The absorbance was measured at 490 nm on a Coulter microplate reader.

Drug potency was expressed by $GI_{50}$ values and calculated by a non-linear regression analysis of the values above and below 50% of the control. The results are summarized in Table 1 below.

TABLE 1

Growth Inhibition ($GI_{50}$) Values (μM) for Cisplatin and Representative Platinum Compounds for Selected Cell Lines.

| PLATINUM COMPOUND | HT29 | HCT-116 | NCI-H69 | NCI-H69/AR | A2780 | A2780/DDPT |
|---|---|---|---|---|---|---|
| Cisplatin | 61 | 43 | 15 | 15 | 15 | 57 |
| DAPTA-diplatinum | >100 | 81 | 27 | 21 | 20 | >100 |
| EGTA-diplatinum | UTD* | >100 | >100 | >100 | >100 | UTD* |
| DTPA-diplatinum | 54 | 41 | 18 | 23 | 19 | 62 |
| TTHA-diplatinum | 53 | 23 | 9.3 | 16 | 7.1 | 48 |

*UTD means Unable to Determine

As shown in Table 1, DTPA-diplatinum and TTHA-diplatinum show potency comparable to or greater than cisplatin in all cell lines.

While illustrative embodiments have been illustrated and described, it will be appreciated that various changes can be made therein without departing from the spirit and scope of the invention.

The invention claimed is:

1. A compound having the structure

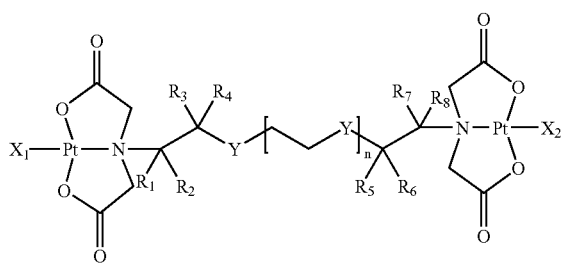

wherein, $R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

Y at each occurrence is independently selected from O and $NR_9$, wherein $R_9$ is selected from hydrogen, substituted and unsubstituted alkyl, and substituted and unsubstituted acyl;

n is 0, 1, 2, 3, 4, or 5; and $X_1$ and $X_2$ are independently selected from ammonia, amino, nitro, C1-C6 alkoxy, hydroxy, chloride, bromide, and iodide.

2. The compound of claim 1, wherein Y is O.

3. The compound of claim 1, wherein Y is N and $R_9$ is selected from $CH_2OH$, $CH_2NH_2$, $CH_2CO_2H$, and $C(=O)$-$nC_{10}H_{21}$-$nC_{17}H_{35}$.

4. The compound of claim 1, wherein $R_1$-$R_8$ are hydrogen.

5. The compound of claim 1, wherein n is 0.

6. The compound of claim 1, wherein $X_1$ and $X_2$ are chloride.

7. The compound of claim 1, wherein alkyl is substituted or unsubstituted $C_1$-$C_7$ alkyl.

8. The compound of claim 1, wherein cycloalkyl is substituted or unsubstituted $C_3$-$C_7$ cycloalkyl.

9. A compound having the structure

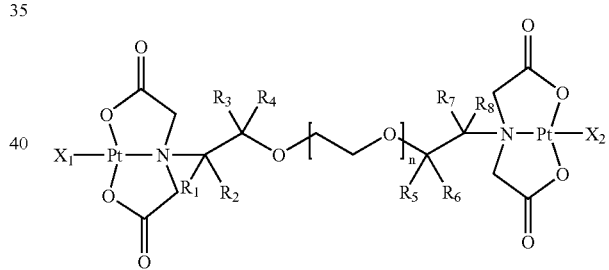

wherein, $R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

n is 0, 1, 2, 3, 4, or 5; and $X_1$ and $X_2$ are independently selected from ammonia, amino, nitro, C1-C6 alkoxy, hydroxy, chloride, bromide, and iodide.

10. The compound of claim 9, wherein $R_1$-$R_8$ are hydrogen.

11. The compound of claim 9, wherein n is 1.

12. A compound having the structure

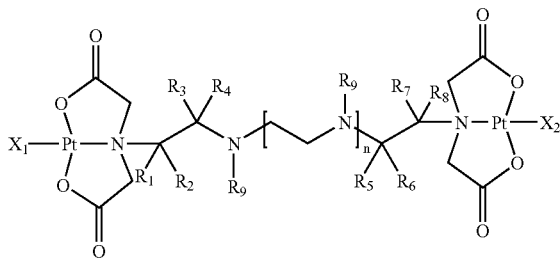

wherein,
$R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

$R_9$ at each occurrence is independently selected from hydrogen and substituted and unsubstituted alkyl, and substituted and unsubstituted acyl;

n is 0, 1, 2, 3, 4, or 5; and $X_1$ and $X_2$ are independently selected from ammonia, amino, nitro, C1-C6 alkoxy, hydroxy, chloride, bromide, and iodide.

13. The compound of claim 12, wherein $R_1$-$R_8$ are hydrogen.

14. The compound of claim 12, wherein $R_9$ is selected from $CH_2OH$, $CH_2NH_2$, $CH_2CO_2H$, and $C(=O)$-$nC_{10}H_{21}$-$nC_{17}H_{35}$.

15. The compound of claim 12, wherein n is 0.

16. The compound of claim 12, wherein n is 1.

17. A compound having the structure

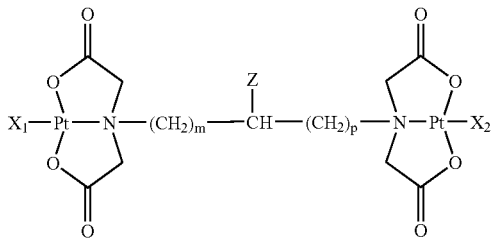

wherein,
m is 1, 2, 3, 4, 5, or 6;
p is 1, 2, 3, 4, 5, or 6;
Z is selected from $OR_{10}$ and $NR_{11}R_{12}$, wherein $R_{10}$, $R_{11}$, and $R_{12}$ are selected from hydrogen and substituted and unsubstituted alkyl; and $X_1$ and $X_2$ are independently selected from ammonia, amino, nitro, C1-C6 alkoxy, hydroxy, chloride, bromide, and iodide.

18. The compound of claim 17, wherein m is 1.
19. The compound of claim 17, wherein p is 1.
20. The compound of claim 17, wherein Z is OH.
21. A compound having the structure

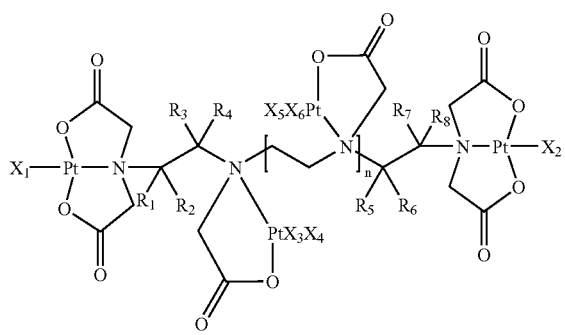

wherein,
$R_1$, $R_2$, $R_3$, $R_4$, $R_5$, $R_6$, $R_7$, and $R_8$ are independently selected from hydrogen, substituted and unsubstituted aryl, substituted and unsubstituted alkyl, and substituted and unsubstituted cycloalkyl, or $R_1$, $R_2$, $R_3$, and $R_4$ together with the carbons atoms to which they are attached form a substituted and unsubstituted benzene ring, or $R_5$, $R_6$, $R_7$, and $R_8$ together with the carbons atoms to which they are attached form a substituted and unsubstituted benzene ring;

n is 0, 1, 2, 3, 4, or 5; and $X_1$, $X_2$, $X_3$, $X_4$, $X_5$, and $X_6$ are independently selected from ammonia, amino, nitro, C1-C6 alkoxy, hydroxy, chloride, bromide, and iodide.

22. The compound of claim 21, wherein $R_1$-$R_8$ are hydrogen.

23. The compound of claim 21, wherein n is 0.

24. The compound of claim 21, wherein n is 1.

25. A pharmaceutical composition, comprising a compound of claim 1 and a pharmaceutically acceptable carrier.

26. The composition of claim 25 further comprising a second anticancer agent.

27. A method for treating a cellular proliferative disease, comprising administering a therapeutically effective amount of a compound of claim 1 to a subject in need thereof.

28. The method of claim 27, wherein the cellular proliferative disease is a hematologic cancer.

29. The method of claim 27, wherein the cellular proliferative disease is a nonhematologic cancer.

* * * * *

UNITED STATES PATENT AND TRADEMARK OFFICE
CERTIFICATE OF CORRECTION

PATENT NO. : 7,268,245 B2  
APPLICATION NO. : 11/550546  
DATED : September 11, 2007  
INVENTOR(S) : M. Lal et al.

It is certified that error appears in the above-identified patent and that said Letters Patent is hereby corrected as shown below:

| COLUMN | LINE | ERROR |
|---|---|---|
| 20 (Claim 7, | 26 Line 2) | "$C_1$-$C_7$" should read --$C_1$-$C_{17}$-- |

Signed and Sealed this

Twentieth Day of May, 2008

JON W. DUDAS  
*Director of the United States Patent and Trademark Office*